United States Patent [19]

Blum

[11] Patent Number: 4,698,447

[45] Date of Patent: Oct. 6, 1987

[54] PROCESS FOR PRODUCTING 10-PHENYL-10H-PHENOXAPHOSHINE

[75] Inventor: David M. Blum, Bergen, N.J.

[73] Assignee: American Cyanamid Company, Stamford, Conn.

[21] Appl. No.: 839,392

[22] Filed: Mar. 14, 1986

[51] Int. Cl.$^4$ ............................................... C07F 9/50
[52] U.S. Cl. .................................................... 568/12
[58] Field of Search ........................................... 568/12

[56] References Cited

U.S. PATENT DOCUMENTS 3,449,426  6/1969  Braye ................................ 568/12 X
3,576,863  4/1971  Strycker .......................... 568/12 X

OTHER PUBLICATIONS

Chemical Abstracts, 77 4475w, (1972).
Chemical Abstracts, 62 11850d, (1965).
Chemical Abstracts, 80 26860g, (1974).

*Primary Examiner*—Helen M. S. Sneed
*Attorney, Agent, or Firm*—H. G. Jackson

[57] ABSTRACT

An improved, simplified process for producing 10-phenyl-10H-phenoxaphosphine in a yield of about 55% comprising reacting n-butyl lithium in a nonpolar hydrocarbon with diphenyl ether in tetramethylethylenediamine and diethyl ether, adding phenyl phosphonous dichloride and then water, and recovering the final product.

6 Claims, No Drawings

PROCESS FOR PRODUCTING 10-PHENYL-10H-PHENOXAPHOSHINE

BACKGROUND OF THE INVENTION

The compound 10-phenyl-10H-phenoxaphosphine having the structure:

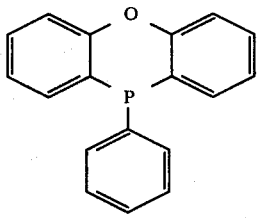

was first disclosed in the literature by F. G. Mann and I. T. Millar, J. Chem. Soc., 3746 (1953) and its biological importance was noted by I. Granoth, et al., Israel J. Chem., 6, 651 (1968).

A simplified, more rapid method for its synthesis was disclosed by I. Granoth, et al., J. Chem. Soc., Perkin Transactions II, Part 1, 697 (1972). That process for the production of 10-phenyl-10H-phenoxaphosphine, illustrated in Flowchart A, consists of reacting n-butyl lithium in a 90% hexane solution with diphenyl ether in a mixture of tetrahydrofuran and ether under a nitrogen atmosphere at reflux for 5 hours, then adding phenylphosphonous dichloride dropwise, stirring the mixture and then adding water dropwise.

FLOWCHART A

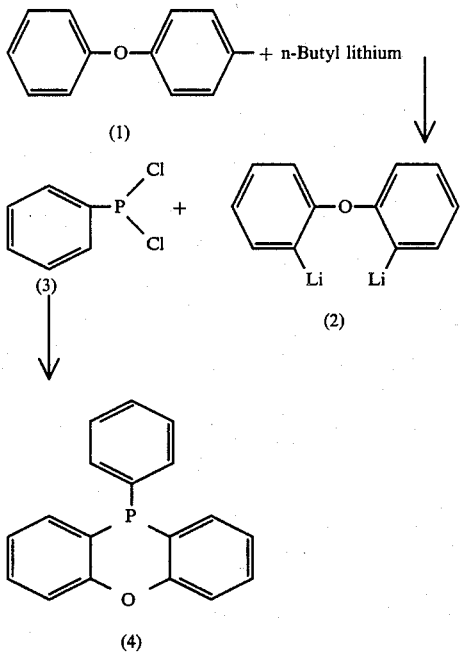

Distillation of the organic layer and crystallization from ethanol give the desired product. The yield obtainable by that method is only 17%, however, so that the process is economically disadvantageous where commercial quantities of the compound are required.

DESCRIPTION OF THE INVENTION

The compound 10-phenyl-10H-phenoxaphosphine is the key starting material used in a reaction to produce a series of highly useful diuretic compounds which are 10-[[(substituted)carbonyl]imino]-10,10-dihydro-10-phenyl-10-H-phenoxaphosphines, which are the subject of application Ser. No. 836,278 filed Mar. 5, 1986.

A method has now been discovered whereby the yield of 10-phenyl-10H-phenoxaphosphine can be raised to 56%, more than triple the yield previously possible.

In the reaction process of the invention, n-butyl lithium is dissolved in a non-polar hydrocarbon solvent. Preferably, the solvent will be a $C_5$–$C_{10}$ hydrocarbon, more preferably a $C_5$–$C_8$ hydrocarbon, and optimally, the solvent will be hexane. The above solution is mixed with a solution of diphenyl ether in tetramethylethylenediamine and diethyl ether under an inert atmosphere.

The use in the reaction of the present invention of tetramethylethylenediamine rather than tetrahydrofuran is the key factor to the sharply increased yields. Although tetramethylethylenediamine has on occasion been used with organolithium reagents, it does not routinely affect the course of the reaction. A change in the yield of the order of magnitude seen in the present invention is, therefore, unexpected as well as advantageous. Optimum yields of 10-phenyl-10-H-phenoxaphosphine are obtained when the molar ratio of tetramethylethylenediamine to diphenyl ether is 2:1. However, the reaction produces significant yields of the desired product at molar ratios of from about 1:1 to about 10:1 of the above two reagents. In the absence of tetramethylethylenediamine, less than 10% of the desired product is obtained.

The reaction is allowed to proceed to completion. At ambient temperature, which is preferred, reaction time is generally from about two hours to about six hours. To recover the final product, phenylphosphonous dichloride is added to the reaction mixture dropwise to avoid overheating the mixture, followed by the addition of an aliquot of water, which is also preferably added slowly for the same reason. The organic layer is separated and concentrated, preferably in vacuo, producing an orange syrup.

Purification of the final product may be achieved by standard methods. For example, the syrup may be distilled over a short path (bp 145°–175° C./0.2 mm), producing a liquid which solidifies on cooling and then crystallized from an organic solvent, e.g., absolute ethanol. Purification of the compound may also be advantageously performed via column chromatography, using, e.g., silica or alumina gels and standard eluants. The following Example, which is not to be construed as limiting the invention, constitutes the preferred embodiment.

EXAMPLE

A 240 ml portion of 2.6 M n-butyl lithium in hexane (0.62 mole) was added to a solution of 51 g (0.3 mole) of diphenyl ether in 69 g (0.6 mole) of tetramethylethylenediamine and 350 ml of diethyl ether under dry argon atmosphere. The resulting mixture was stirred at ambient temperature for 5 hours and then 54 g (0.3 mole) of phenylphosphonous dichloride was added dropwise over about one hour. A 150 ml portion of water was added slowly and the organic layer was separated and then concentrated in vacuo to an orange syrup. Short path distillation, bp 145°–175° C./0.2 mm, gave a liquid which solidified upon cooling. Crystallization from absolute ethanol gave 46 g of the desired product, mp 97°–97° C., yield 56%.

What is claimed is:

1. In a process for producing 10-phenyl-10-$\underline{H}$-phenoxaphosphine, by
   (1) mixing n-butyl lithium dissolved in $C_5$–$C_{10}$ hydrocarbon with a solution of diphenyl ether in diethyl ether under an inert atmosphere;
   (2) adding phenylphosphonous dichloride;
   (3) adding water; and
   (4) recovering and purifying the final product from the organic phase the improvement comprising the use of tetramethylethylenediamine in the solution of diphenyl ether and diethyl ether.

2. A process according to claim 1, wherein the molar ratio of tetramethylethylenediamine to diphenyl ether is from about 1:1 to about 10:1.

3. A process according to claim 1, wherein the molar ratio of tetramethylethylenediamine to diphenyl ether is 2:1.

4. A process according to claim 1 wherein the product is recovered and purified from the organic phase by distillation and crystallization from an organic solvent.

5. A process according to claim 1 wherein the product is recovered and purified from the organic phase by column chromatography.

6. A process according to claim 1 wherein the yield of the final product is greater than 50%.

* * * * *